(12) United States Patent
Rosenberg

(10) Patent No.: US 10,716,635 B2
(45) Date of Patent: Jul. 21, 2020

(54) VACUUM IMMOBILIZER FOR SURGICAL ROBOTIC CARTS

(71) Applicant: Covidien LP, Mansfield, MA (US)

(72) Inventor: Meir Rosenberg, Newton, MA (US)

(73) Assignee: Covidien LP, Mansfield, MA (US)

( * ) Notice: Subject to any disclaimer, the term of this patent is extended or adjusted under 35 U.S.C. 154(b) by 24 days.

(21) Appl. No.: 16/081,971

(22) PCT Filed: Feb. 27, 2017

(86) PCT No.: PCT/US2017/019568
§ 371 (c)(1),
(2) Date: Sep. 4, 2018

(87) PCT Pub. No.: WO2017/151450
PCT Pub. Date: Sep. 8, 2017

(65) Prior Publication Data
US 2019/0090964 A1    Mar. 28, 2019

Related U.S. Application Data

(60) Provisional application No. 62/303,418, filed on Mar. 4, 2016.

(51) Int. Cl.
*A61B 50/13* (2016.01)
*A61B 90/50* (2016.01)
*A61B 34/30* (2016.01)
*B25J 5/00* (2006.01)
*A61B 50/20* (2016.01)
(Continued)

(52) U.S. Cl.
CPC .............. *A61B 34/30* (2016.02); *A61B 50/13* (2016.02); *A61B 50/20* (2016.02); *A61B 90/50* (2016.02); *B25J 5/007* (2013.01); *A61B 2017/00535* (2013.01); *A61B 2560/0437* (2013.01); *B62B 5/049* (2013.01)

(58) Field of Classification Search
CPC ...................................................... B62B 5/049
USPC ....................................................... 280/763.1
See application file for complete search history.

(56) References Cited

U.S. PATENT DOCUMENTS 2,009,721 A * 7/1935 Williams ................ B60R 9/058
    160/DIG. 13
2,360,874 A * 10/1944 Herold .................... B62B 5/049
    188/5
(Continued)

FOREIGN PATENT DOCUMENTS

WO    2015142810 A1    9/2015

OTHER PUBLICATIONS

International Search Report and Written Opinion corresponding to counterpart Int'l Appln. No. PCT/US2017/019568 dated Jun. 5, 2017.

(Continued)

*Primary Examiner* — Emma K Frick
(74) *Attorney, Agent, or Firm* — Carter, DeLuca & Farrell LLP

(57) ABSTRACT

A surgical robotic cart assembly includes a vertical column supporting a robotic arm thereon, a base, and a plurality of casters attached to the base and adapted to allow the surgical robotic assembly to move. The surgical robotic cart further includes at least one vacuum cup on the base for sealingly engaging the base to the floor thereby immobilizing the surgical robotic cart assembly.

15 Claims, 5 Drawing Sheets

(51) Int. Cl.
*A61B 17/00* (2006.01)
*B62B 5/04* (2006.01)

(56) References Cited

U.S. PATENT DOCUMENTS

| | | | | |
|---|---|---|---|---|
| 2,941,626 | A | | 6/1960 | Heiden |
| 2,945,242 | A | * | 7/1960 | Heiden ................ A61G 7/1019 188/5 |
| 3,878,573 | A | * | 4/1975 | Boudewyn ............... A61G 7/05 248/362 |
| 3,910,620 | A | * | 10/1975 | Sperry .................. B25B 11/007 248/362 |
| 4,181,297 | A | * | 1/1980 | Nichols ................ A61F 5/3761 128/878 |
| 5,323,879 | A | * | 6/1994 | Poulin .................... B62B 5/049 188/19 |
| 5,366,231 | A | * | 11/1994 | Hung ...................... A47C 7/006 16/44 |
| 6,425,565 | B1 | * | 7/2002 | Montague ............... F16B 47/00 248/205.9 |
| 6,708,706 | B1 | | 3/2004 | Robinson |
| 7,216,399 | B2 | | 5/2007 | Webster et al. |
| 7,886,380 | B2 | * | 2/2011 | Hornbach ............ A47C 19/045 5/613 |
| 9,532,656 | B2 | * | 1/2017 | Johnson .............. B60B 33/0089 |
| 9,844,868 | B1 | * | 12/2017 | Abbey .................... B25D 17/32 |
| 10,123,842 | B2 | * | 11/2018 | Iceman ..................... B25J 5/007 |
| 10,231,792 | B2 | * | 3/2019 | Shiels .................... A61B 34/30 |
| 2006/0254834 | A1 | * | 11/2006 | Dassler .................... A61G 7/08 180/11 |
| 2007/0135779 | A1 | | 6/2007 | Lalomia et al. |
| 2009/0024142 | A1 | | 1/2009 | Ruiz Morales |
| 2009/0085317 | A1 | | 4/2009 | Livengood et al. |
| 2010/0043137 | A1 | | 2/2010 | Zavan |
| 2014/0076827 | A1 | * | 3/2014 | Jiang ...................... A47B 96/00 211/13.1 |
| 2014/0352103 | A1 | | 12/2014 | Won et al. |
| 2017/0087730 | A1 | * | 3/2017 | Robinson ............... A61B 50/13 |
| 2018/0346008 | A1 | * | 12/2018 | Nahum .................. B62B 5/0433 |
| 2019/0024392 | A1 | * | 1/2019 | Naccarato ........... E04F 21/1872 |

OTHER PUBLICATIONS

Extended European Search Report for application No. 17760517.7 dated Sep. 18, 2019.

* cited by examiner

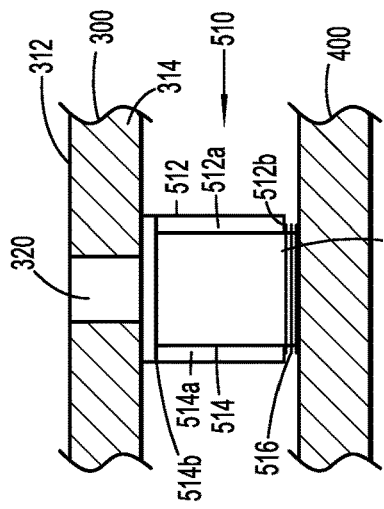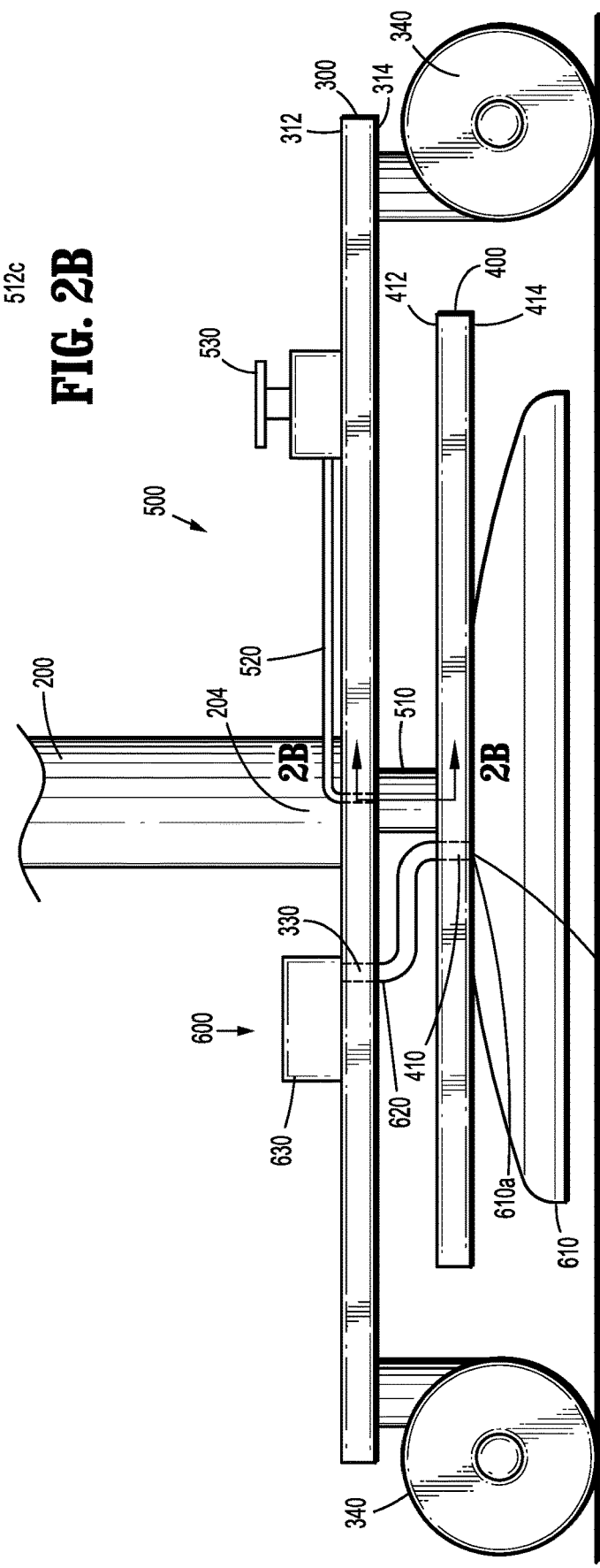

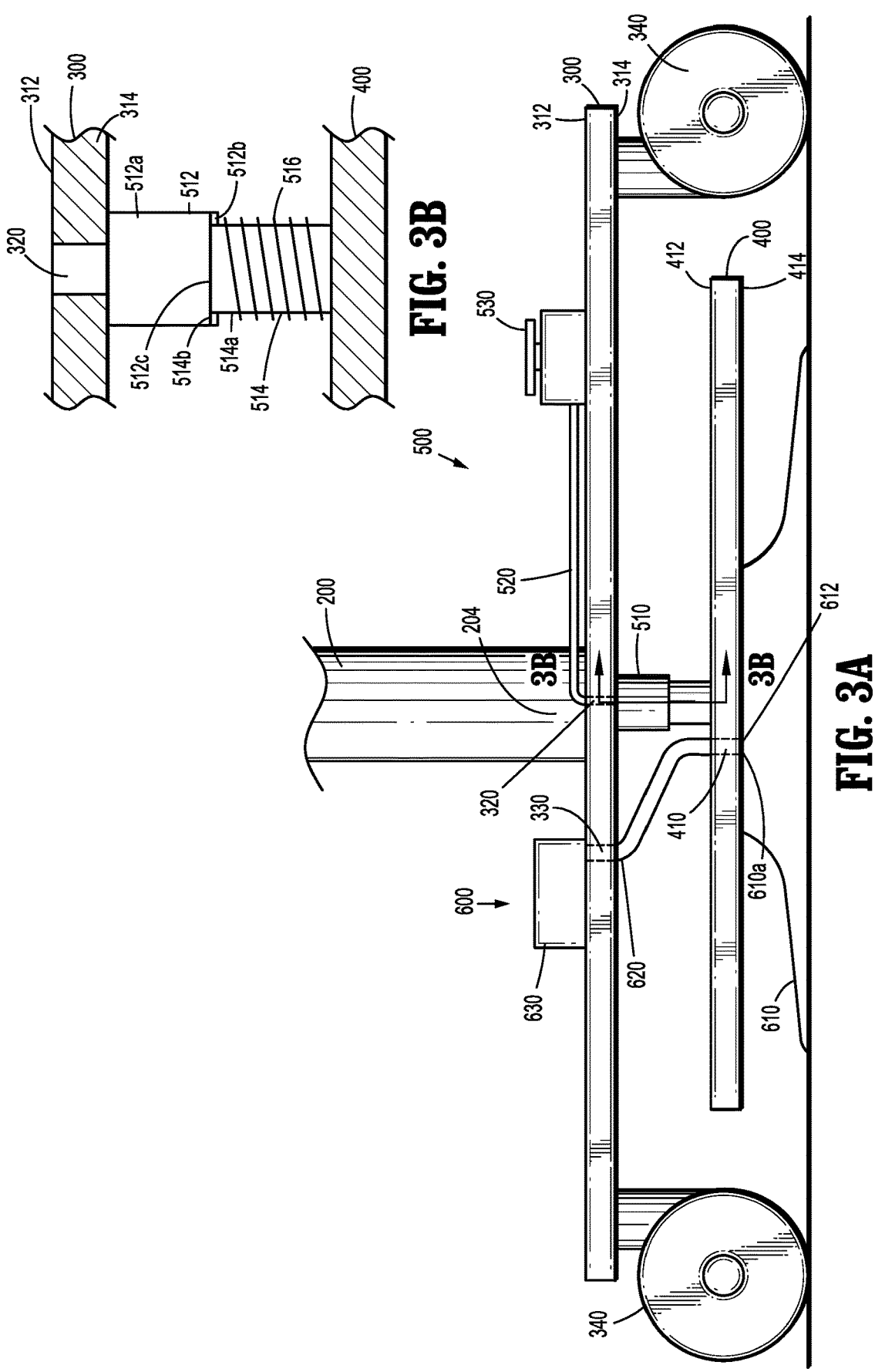

VACUUM IMMOBILIZER FOR SURGICAL ROBOTIC CARTS

CROSS-REFERENCE TO RELATED APPLICATIONS

This application is a U.S. National Stage Application filed under 35 U.S.C. § 371(a) of International Patent Application Serial No. PCT/US2017/019568, filed Feb. 27, 2017, which claims the benefit of and priority to U.S. Provisional Patent Application Ser. No. 62/303,418, filed Mar. 4, 2016, the entire disclosure of which is incorporated by reference herein.

BACKGROUND

Surgical robotic systems are used in minimally invasive medical procedures because of their increased accuracy and expediency. In surgical robotic systems, a robot arm supports a surgical instrument having an end effector mounted thereto by a wrist assembly. In operation, the robot arm inserts, or holds, the surgical instrument within in a small incision via a surgical portal or a natural orifice of a patient to position the end effector at a working site within a patient's body.

Most of the surgical robotic systems on the market are heavy and stationary requiring a pallet jack to be relocated. In some of the more modern surgical robotic systems, the robot arm is supported on a movable surgical robotic cart assembly having a base portion with a set of casters. This is beneficial because the surgical robotic systems can be moved between various rooms as needed without a pallet jack.

However, minimally invasive medical procedures require a high degree of accuracy, precision, and speed, and, therefore, movable surgical robotic systems used for minimally invasive medical procedures need to be precisely immobilized before an operation begins. Accordingly, there is a need to precisely immobilize a surgical robotic cart assembly.

SUMMARY

The present disclosure is directed to a surgical robotic cart immobilizer for mobile surgical robotic systems to stabilize a surgical robotic system before operation.

In accordance with an embodiment of the present disclosure, a surgical robotic cart assembly includes a base, the base being configured to support a robotic arm thereon. The assembly further includes a plurality of casters attached thereto to allow the surgical robotic cart assembly to move along a floor without the need for a pallet jack. At least one vacuum cup is coupled to the base of the assembly and an actuator is configured to move the assembly towards the floor to engage the at least one vacuum cup with the floor. A vacuum source is in fluid communication with the at least one vacuum cup and configured to remove air from the at least one vacuum cup thereby securing the at least one vacuum cup to the floor, when the at least one vacuum is in contact with the floor, and immobilizing the surgical robotic cart assembly.

The immobilization assembly may further include a pedal switch to actuate the actuator.

A first actuation of the pedal switch may move the at least one actuator from a first position to a second position thereby lowering the assembly relative to the floor and placing each vacuum cup in contact with the floor. When each vacuum cup is in contact with the floor, actuation of the vacuum source sealingly engages each vacuum cup thereto.

A second actuation of the pedal switch may move the actuator from the second position to the first position thereby lifting the at least one vacuum cup away from the floor.

The surgical robotic cart assembly may further include a biasing member interposed between the base and the at least one vacuum cup. The biasing member may be configured to urge the at least one vacuum cup towards the base.

In accordance with another embodiment of the present disclosure, the immobilization assembly further includes a vacuum manifold coupled to the at least one vacuum cup in fluid communication with the vacuum source via the vacuum manifold.

The plurality of vacuum cups may be disposed over the perimeter of the base.

The plurality of vacuum cups may be disposed randomly over the base.

When the at least one vacuum cup is in contact with the floor, actuation of the vacuum source sealingly engages the at least one vacuum cup to the floor.

The surgical robotic cart assembly may be immobile when the at least one vacuum cup is sealingly engaged to the floor.

In accordance with another embodiment of the present disclosure, a surgical robotic cart assembly includes a first base portion and a second base portion, the second base portion being secured to the first base portion by at least one hydraulic actuator. An immobilization assembly having a vacuum source and at least one vacuum cup coupled to the second base portion. The at least one vacuum cup being in fluid communication with the vacuum source. The vacuum source is configured to remove air from the at least one vacuum cup, when the at least one vacuum is in contact with the floor, and sealingly engage the at least one vacuum cup to a floor thereby immobilizing the surgical robotic cart assembly.

The immobilization assembly may further include a pedal switch to actuate the hydraulic actuator. The pedal switch may move the at least one hydraulic actuator from the second position towards the first position to thereby lift the second base portion relative to the floor and to move each vacuum cup away from the floor The at least one vacuum cup may be coupled to a second surface of the second base portion.

A first actuation of the pedal switch may move the at least one hydraulic actuator from a first position to a second position thereby lowering the second base portion relative to the floor and placing the at least one vacuum cup in contact with the floor. When the at least one vacuum cup is in contact with the floor, actuation of the vacuum source sealingly engages the at least one vacuum cup to the floor.

A second actuation of the pedal switch may move the at least one hydraulic actuator from the second position to the first position thereby lifting the second base portion relative to the floor and moving the at least one vacuum cup away from the floor.

According to another aspect of the present disclosure, a method of immobilizing a surgical robotic cart assembly includes providing a surgical robotic cart assembly comprising a first base portion and a second base portion. The second base portion being secured to the first base portion by at least one actuator. The first base portion further including at least three casters adapted to allow the surgical robotic cart assembly to move. The surgical robotic cart assembly further including an immobilization assembly coupled to the first and second base portions. The immobilization assembly includes a vacuum source and at least one vacuum cup in fluid communication with each other, the at least one vacuum cup is coupled to the second base portion and then placing the at least one vacuum cup in contact with a floor to immobilize the surgical robotic cart assembly.

The method may include placing the at least one vacuum cup in contact with the floor by activating the actuator thereby moving the at least one actuator from a first position to a second position to place the at least one vacuum cup in contact with the floor.

The method may include activating the vacuum source to sealingly engage the at least one vacuum cup to the floor. When the at least one vacuum cup is sealingly engaged with the floor, the surgical robotic cart assembly is immobile.

The method may include deactivating the at least one actuator and moving the at least one hydraulic actuator from the second position to the first position thereby lifting the second base portion relative to the floor and moving the at least one vacuum cup away from the floor.

According to an aspect of the present disclosure, the method may include activating the vacuum source, in reverse, to blow air from the at least one vacuum cup, against the floor, to move the surgical robotic cart assembly away from the floor.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of exemplary embodiment(s) given below, serve to explain the principles of the disclosure, wherein:

FIG. 2A is a front, elevational view of the surgical robotic cart of FIG. 1 illustrating a second base portion and a vacuum cup thereof positioned away, or separated from the floor;

FIG. 2B is a side, cross-sectional view of an actuator of FIG. 2A, taken along section line 2B-2B of FIG. 2A, illustrating a plunger of the actuator in a retracted position;

FIG. 3A is a front, elevational view of the surgical robotic cart of FIG. 1 illustrating the second base portion and the vacuum cup thereof sealingly engaged to the floor;

FIG. 3B is a side, cross-sectional view of the actuator of FIG. 3A, taken along section line 3B-3B of FIG. 3A, illustrating the plunger of the actuator in an extended position;

DETAILED DESCRIPTION

Figure 1:
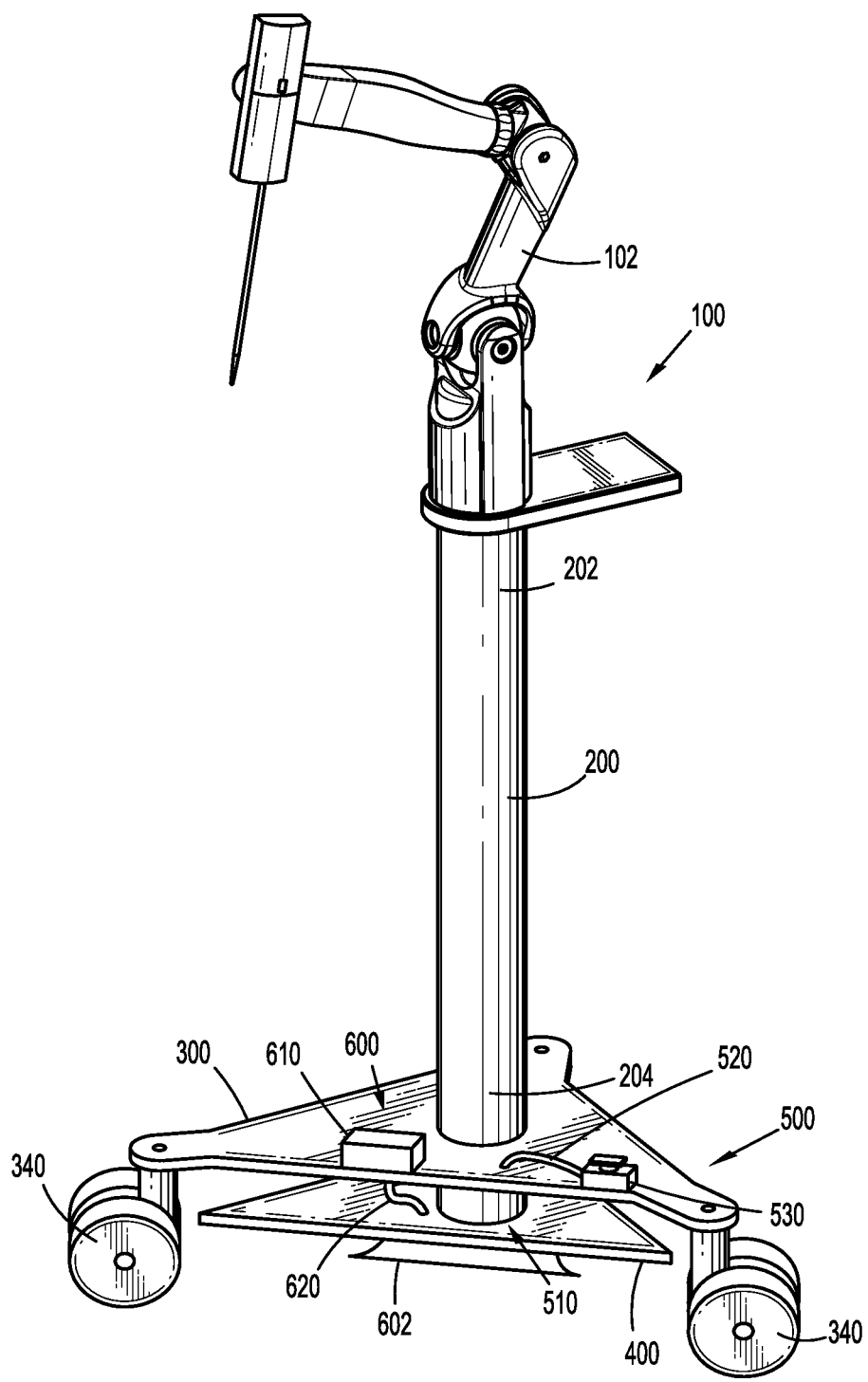
FIG. 1 is a perspective view of a surgical robotic cart having an immobilization assembly in accordance with the present disclosure.

Embodiments of the present disclosure are described in detail with reference to the drawings, in which like reference numerals designate identical or corresponding elements in each of the several views.

With reference to FIG. 1, one exemplary embodiment of a surgical robotic cart assembly configured for use in accordance with the present disclosure is generally identified as 100, although it is also envisioned that the aspects and features of the present disclosure may be similarly incorporated into any suitable surgical robotic cart assembly. Surgical robotic cart assembly 100 generally includes a robotic arm 102, a vertical column 200, a first base portion 300, and a second base portion 400. Robotic arm 102 is attached to a first end 202 of vertical column 200 and first base portion 300 is attached to a second end 204 of vertical column 200. First base portion 300 includes a plurality of casters 340 coupled thereto. Each of the casters 340 is configured to swivel and allow surgical robotic cart assembly 100 to move.

As shown in FIGS. 1-3B, first base portion 300 and second base portion 400 are connected via an actuation assembly generally identified as 500. It is envisioned that actuation assembly 500 may define a variety of actuator types, such as, for example, electrical actuators, pneumatic actuators, hydraulic actuators, piezo actuators, venturi vacuums, etc., any of which may be connected to first base portion 300 and second base portion 400. Actuation assembly 500 may alternatively, or additionally, include a mechanical or manual actuation mechanism, such as, for example, a motor on a crank mechanism, a hand crank, crank rocker mechanism, etc. In the interest of brevity, actuation assembly 500 will be discussed herein with reference to a hydraulic actuator 510.

Hydraulic actuator 510 of hydraulic actuation assembly 500 is configured to move between an extended, first position, and a retracted, second position. As shown in FIGS. 2B and 3B, hydraulic actuator 510 has an outer member 512 (e.g., cylinder) and an inner member 514 (e.g. piston).

Outer member 512 of hydraulic actuator 510 forms a cavity 512a, an aperture 512b, and a lip 512c. Lip 512c extends inwardly and is dimensioned to allow a portion of inner member 514 to pass through aperture 512b. Inner member 514 forms a body 514a and a plunger 514b. Body 514a of inner member 514 is dimensioned to pass through aperture 512b of outer member 512. Plunger 514b is dimensioned to sealingly engage cavity 512a of outer member 512 and is larger than aperture 512b, thereby preventing inner member 514 from passing through aperture 512b.

It is contemplated that actuation assembly 500 may include a biasing member 516. With reference to hydraulic actuator 510, biasing member 516 may be disposed about a circumference of the inner member 514 between and connected to each of lip 512c of outer member 512 and a first surface 412 of second base portion 400. Biasing member 516 is configured to hold second base portion 400 near first base portion 300, thereby maintaining a vacuum cup 610 of an immobilization assembly 600 spaced away from a floor surface. Biasing member 516 additionally assists in raising second base portion 400 away from the floor surface, as biasing member 516 exerts a retracting force on second base portion 400, as discussed below.

Referring back to FIGS. 2A and 3A, first base portion 300 of surgical robotic cart 100, defines a first surface 312 and a second surface 314. First base portion 300 further defines a hydraulic port 320 that is formed between first surface 312 and second surface 314. Hydraulic actuator 510 is coupled to first base portion 300 such that hydraulic port 320 opens into cavity 512a of outer member 512 of hydraulic actuator 510.

Actuation assembly 500 further includes a hydraulic tube 520 and a pedal switch 530. Pedal switch 530 is coupled to first surface 312 of first base portion 300 and hydraulic tube 520 interconnects pedal switch 530 and hydraulic port 320. Pedal switch 530 is configured to move between an extended, or unactuated position, and a depressed, or actuated position. Pedal switch 530 may have an internal locking mechanism (not shown) that holds pedal switch 530 in the actuated position. When the operator wants to move pedal switch 530 from the actuated to the unactuated position, the operator may depress pedal switch 530 to disengage the locking mechanism which allows pedal switch 530 to move to the unactuated position.

Now referring to FIGS. 2B and 3B, actuation assembly 500 further includes a fluid 518 between pedal switch 530 and hydraulic actuator 510. Fluid 518 may be any suitable non-compressible fluid including water or oil. In operation, when pedal switch 530 is moved from the unactuated position to the actuated position, pressure is applied to fluid 518 of actuation assembly 500. The increase in pressure on fluid 518 causes fluid 518 to apply pressure onto plunger 514b of inner member 514 of hydraulic actuator 510 and extend plunger 514b from outer member 512. As plunger 514b extends from outer member 512, biasing member 516 may be overcome, such that inner member 514 moves towards the floor. As a result, second base portion 400 of surgical cart assembly 100 is lowered towards the floor. The pressure threshold to move hydraulic actuator 510 into the expanded, second position, depends on a spring constant of biasing member 516. As mentioned above, pedal switch 530 may include an internal locking mechanism (not shown) that can hold pedal switch 530 in the actuated position. When pedal switch 530 is held in the actuated position, hydraulic actuator 510 is held in the extended, second position.

With reference to FIGS. 2A-3B, surgical robotic cart assembly 100 further includes an immobilization assembly, shown generally as reference numeral 600. Immobilization assembly 600 includes a vacuum cup 610 defining an aperture 612 attached to a vacuum port 410 formed in second base portion 400. Vacuum cup 610 moves into and out of contact with a surface of a floor beneath surgical robotic cart assembly 100, as discussed below A vacuum tube 620 interconnects vacuum port 410 of second base portion 400 and a vacuum port 330 defined between first and second surfaces 312, 314 of first base portion 300. Immobilization assembly 600 further includes a vacuum source or pump 630 coupled to the first surface 312 of the first base portion 300 and vacuum tube 620. Vacuum source 630 may be positioned on first base portion 300 such that it is in fluid communication with vacuum port 330 of first base portion 300. Once vacuum cup 610 is in contact with the floor beneath the surgical robotic cart assembly 100, and a fluid tight seal formed therebetween, immobilization assembly 600 facilitates the evacuation of air from vacuum cup 610 such that suction is created and maintained between the vacuum cup 610 and the floor.

Referring now to FIGS. 3A and 3B, in operation, an operator moves surgical robotic cart assembly 100 into a desired position, and then depresses pedal switch 530 from the unactuated position to the actuated position, thereby moving hydraulic actuator 510 from the retracted, first position, to the extended, second position. Moving hydraulic actuator 510 into the second position lowers second base portion 400 towards the floor and places vacuum cup 610 in contact therewith. With pedal switch 530 locked into place, holding the hydraulic actuator 510 in the second position, vacuum cup 610 is held against the floor. With vacuum cup 610 held against the floor, the operator then activates vacuum source 630, removing air from vacuum cup 610, and sealingly engaging vacuum cup 610 to the floor. Once vacuum cup 610 is sealingly engaged to the floor, surgical robotic cart assembly 100 is immobilized and held in a fixed position. Vacuum source 630 may then be deactivated. Alternatively, a feedback or sensor system (not shown) may be provided which monitors the vacuum between vacuum cup 610 and the floor, and cycles vacuum source 630 on and off, as needed, to maintain the vacuum therebetween.

Once the operator is ready to move surgical robotic cart assembly 100, with vacuum source 630 turned off, pedal switch 530 is again actuated, disengaging the locking mechanism thereof, and moving pedal switch 530 into the unactuated position. As pedal switch 530 moves from the actuated position towards the unactuated position, hydraulic actuator 510 moves from the extended, second position, towards the retracted, first position, due to a retraction of biasing member 516, thereby lifting second base portion 400 away from the floor and breaking the seal between vacuum cup 610 and the floor. Once the seal is broken between vacuum cup 610 and the floor, vacuum cup 610 can lift away from the floor, allowing surgical robotic cart assembly 100 to move.

Figure 4:
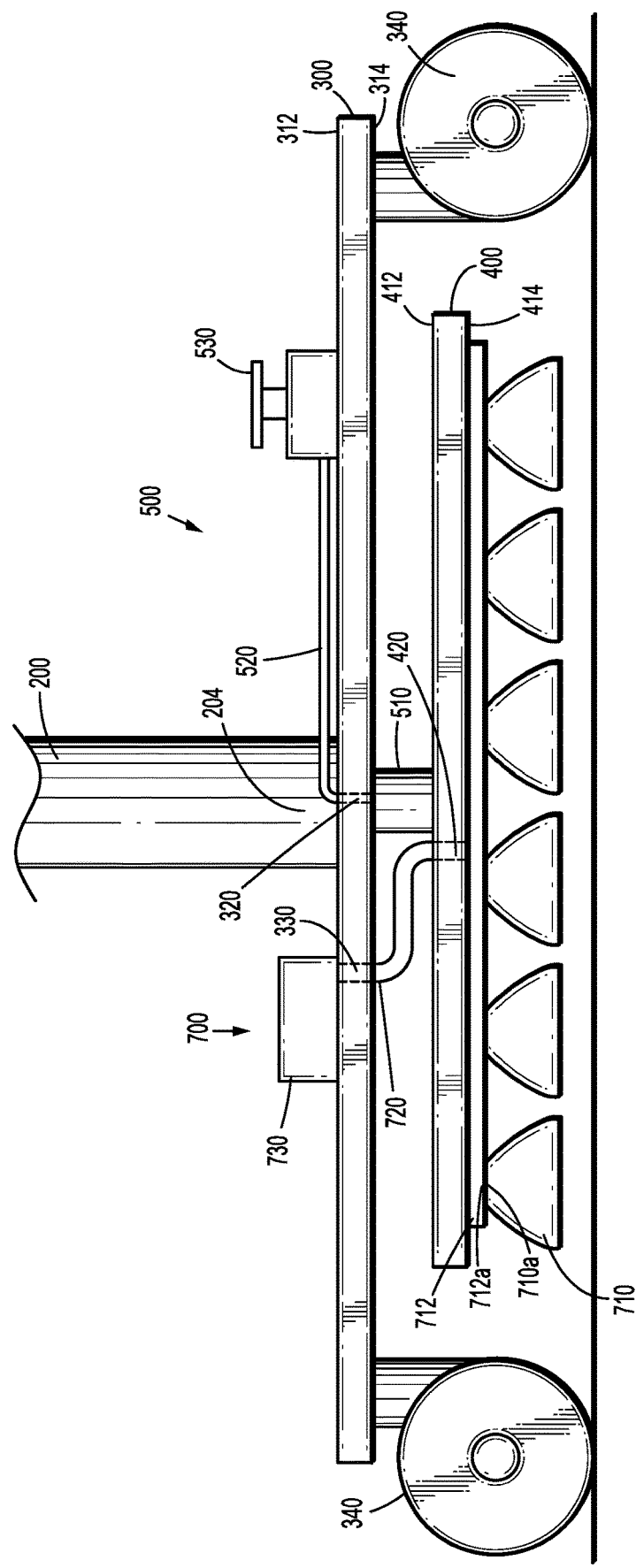
FIG. 4 is a front, elevational view of an alternative embodiment of a surgical robotic cart having an immobilization assembly in accordance with the present disclosure.
Figure 5:
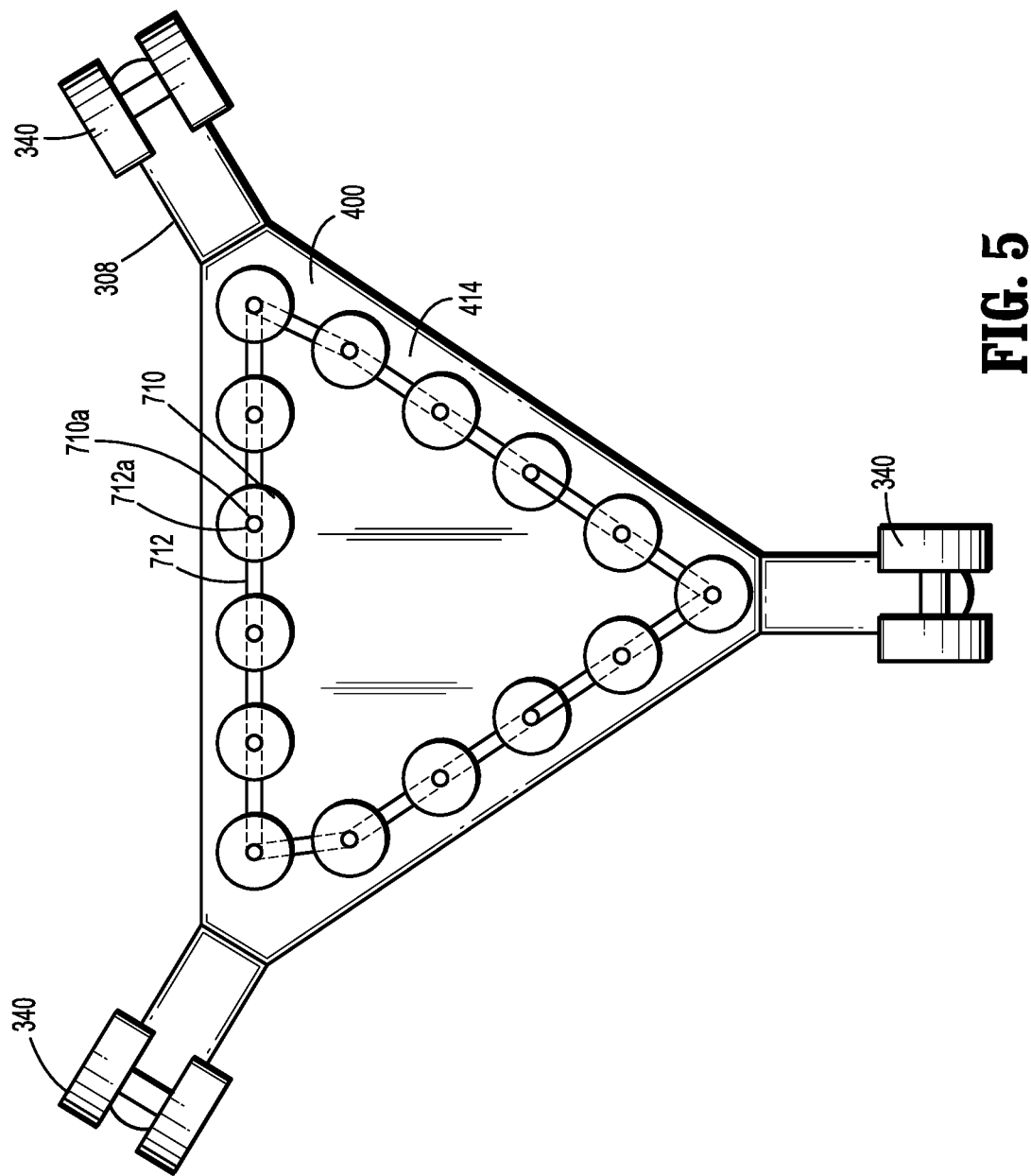
FIG. 5 is a bottom, elevational view of the surgical robotic cart of FIG. 4, illustrating the immobilization assembly having a plurality of vacuum cups coupled to a vacuum manifold.

FIGS. 4 and 5 illustrate an alternative embodiment of a surgical robotic cart assembly configured for use in accordance with the present disclosure having an alternative immobilization assembly generally identified by reference numeral 700. Immobilization assembly 700 is similar to immobilization assembly 600 except that immobilization assembly 700 includes a plurality of vacuum cups 710 rather than a single vacuum cup 610. Accordingly, surgical cart assembly 100 is configured such that immobilization assemblies 600 and 700 may be interchangeable.

Each of the plurality of vacuum cups 710 define an aperture 710a, where each vacuum cup 710 is coupled to a vacuum manifold 712 at its respective aperture 710a. Vacuum manifold 712 is coupled to second surface 414 of the second base portion 400 and is in fluid connection with vacuum port 420 of the second base portion 400. Vacuum manifold 712 may be a tubular member having a plurality of apertures 712a, where each aperture of the plurality of apertures 712a is coupled to a respective aperture 710a of each vacuum cup of the plurality of vacuum cups 710. Vacuum manifold 712 may be formed into any suitable shape, including a grid or a loop positioned along the perimeter of the second surface 414 of second base portion 400 (FIG. 5), thereby covering the perimeter of the second surface 414 of the second base portion 400 with vacuum cups 710. Alternatively vacuum cups 710 may cover substantially the entire second surface 414 of second base portion 400 (not shown) with each vacuum cup being in fluid communication with vacuum manifold 712.

In operation, an operator moves surgical robotic cart assembly 100 into position and then depresses pedal switch 530, moving hydraulic actuator 510 from the retracted, first position, to the extended, second position. When hydraulic actuator 510 moves from the first position to the second position, base portion 400 simultaneously moves towards the floor, thereby placing the plurality of vacuum cups 710 in to contact with the floor. Pedal switch 530 may then be locked into place holding the plurality of vacuum cups 710 against the floor. With the plurality of vacuum cups 710 in contact with the floor, the operator activates vacuum source 730 to evacuate the air between the plurality of vacuum cups 710 and the floor, through vacuum manifold 712, thereby sealingly engaging at least one of the plurality of vacuum cups 710 to the floor. Once at least one vacuum cup of the plurality of vacuum cups 710 is sealingly engaged to the floor, surgical robotic cart assembly 100 is immobile and vacuum source 730 may be deactivated. It should be appreciated that although vacuum source 730 may be deactivated, vacuum cups 710 remain sealingly engaged to the floor. Alternatively, a feedback or sensor system (not shown) may be provided which monitors the vacuum between vacuum cups 710 and the floor, and cycles vacuum source 730 on and off, as needed, to maintain the vacuum within vacuum cups 710.

Once the operator is ready to move surgical robotic cart assembly 100, with vacuum source 730 turned off, pedal switch 530 is again actuated, disengaging the locking mechanism thereof, and moving it into the unactuated position. As pedal switch 530 moves from the actuated position towards the unactuated position, hydraulic actuator 510 moves from the extended, second position, towards the retracted, first position, due to a retraction of biasing member 516, thereby lifting second base portion 400 away from the floor. The lifting force from the hydraulic actuator 510 onto second base portion 400 breaks the seal between the plurality of vacuum cups 710 and the floor. When the seal between the plurality of vacuum cups 710 and the floor is broken, the plurality of vacuum cups 710 may be lifted away from the floor, allowing surgical robotic cart assembly 100 to move. It is envisioned that even if the seal between the floor and any individual vacuum cup 710, or a number of vacuum cups 710, is compromised, the fixation of surgical robotic cart assembly 100 to the floor may be maintained through the vacuum seal of the remaining vacuum cups 710.

It is contemplated that vacuum cup 610 and vacuum cups 710, respectively, include material characteristics and mechanical features to increase the capability of establishing and maintaining a vacuum seal with the floor, such that surgical robotic cart assembly 100 is secured thereto. Vacuum cups 610, 710 may be fabricated by, for example, injection molding, from materials such as, for example, silicone or plastic. Specifically, vacuum cups 610, 710 may be constructed from any material know in the art to creation and maintain an airtight seal with the surface of the floor, while maintain rigidity such that vacuum cups 610, 710 are not deformed under suction. It should be appreciated that vacuum cups 610, 710 are configured to sealingly engage with a variety of envisioned floor types, each having respective surface features which may inhibit airtight sealing therebetween. Vacuum cups 610, 710 may further defined mechanical features, such as, for example, ribs, struts, or other reinforcement features (not shown), such that physical deformation during the evacuation of air is inhibited. Such reinforcement features may include, for example, lateral struts, longitudinal struts, or concentric rings disposed on an outer surface, an inner surface, or molded therebetween. Vacuum cups 610, 710 are additionally configured to prevent damage to the floor during fixation thereto, including such features as, for example, the means to disburse contact and surface forces between vacuum cups 610, 710 and the floor. Vacuum cups 610, 710 may further include ribs (not shown) disposed radially inward from an inner surface thereof, or alternatively extending across an opening of vacuum cups 610, 710, respectively, such that the ribs are in contact with the surface of the floor and act to prevent bulging, buckling, and/or lifting of the floor during fixation thereto. Vacuum cups 610, 710 may further define a variety of sizes such that the desired fixation is achieved. With respect to immobilization assembly 700, the plurality of vacuum cups 710 may be uniformly or non-uniformly sized.

Surgical robotic cart assembly 100 may further include safety or redundancy features to inhibit a failure of immobilization assemblies 600, 700, and/or indicate a deficiency when seeking fixation. Surgical robotic cart assembly 100 may include a pressure sensor configured to determine if the vacuum between vacuum cups 610, 710 and the floor is not achieved and/or is weakening. A loss of vacuum may develop due to an air leakage between the floor and vacuum cups 610, 710, and/or a leak between vacuum cups 610, 710 and vacuum sources 630, 730, respectively. The pressure sensor may be configured to provide an indication to the user of such a leak and/or automatically cycle vacuum source 630, 730 to re-establish the vacuum. The pressure sensor may additionally be configured to indicate the creation of a successful vacuum during setup. Such a sensor may provide an audible, visual, or any other desired indication to a user. With respect to immobilization assembly 700, it is envisioned that the pressure sensor may be further configured to indicate which vacuum cups, respectively, out of the plurality of vacuum cups 710 are failing.

It is envisioned that surgical robotic cart assembly 100 may include safety or redundancy features to quickly facilitate the release of vacuum cups 610, 710 from the floor. In an emergency situation, movement of surgical robotic cart assembly 100 may be expeditiously required, such that the method of releasing vacuum cups 610, 710 described herein must be circumvented. To urgently break the sealing engagement between vacuum cups 610, 710 and the floor, a release valve, pull tab, vent, and/or any other pressure release mechanism known in the art may be disposed on vacuum cups 610, 710, and/or in line between vacuum cups 610, 710 and vacuum source 630, 730, respectively. It is envisioned that an emergency release switch may be disposed in close proximally to, and/or easily accessible by, the operator to achieve the quick release of vacuum cups 610, 710 from the floor.

Surgical robotic cart assembly 100 may further include one or more torque sensors, accelerometers, or other sensors disposed thereon and configured to determine the center of gravity of surgical robotic cart assembly 100. It is envisioned that such sensors may be disposed on the robotic arm 102 and/or vertical column 202, such that the stability of surgical robotic cart assembly 100 may be calculated and maintained during use and articulation thereof. It should be appreciated that during articulation of robotic arm 102, the center of gravity of surgical robotic cart assembly 100 will be dynamic. In the event the center of gravity of surgical robotic cart assembly 100 is brought beyond the capability of immobilization assemblies 600, 700 to fix surgical robotic cart assembly 100 to the floor, it is envisioned that an alarm will sound for the user. It is further envisioned that such a safety feature may be configured to automatically inhibit articulating of robotic arm 102 beyond an indicated and/or calculated center of gravity of surgical robotic cart assembly 100.

According to an aspect of the present disclosure, it is contemplated that vacuum sources 630, 730 may be operated in reverse (e.g., to blow or expel air therefrom), wherein the air is directed towards the ground or floor. It is further contemplated, that in certain embodiments, that vacuum sources 630, 730 may be replaced by or supplemented with dedicated blower sources. It is further contemplated that baffles, cushions, walls or the like may extend from second base portion 400 of surgical robotic cart assembly 100. For example, the baffles, cushions, walls may extend around the periphery of second base portion 400 to form a perimeter therearound. Accordingly, in operation, when vacuum sources 630, 730 are operated to expel air, a cushion of air may be formed between surgical robotic cart assembly 100 and the floor, effectively lifting surgical robotic cart assembly 100 off the floor (e.g., hover) and permitting movement of surgical robotic cart assembly 100 along the floor to transporting and locating purposes.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the claimed invention. Therefore, the above description should not be construed as limiting, but merely as exemplifications of particular embodiments. Those skilled in the art will envision other modifications within the scope and spirit of the claims appended hereto.

What is claimed is:

1. A surgical robotic cart assembly supported on a floor, the surgical robotic cart assembly comprising:
    a first base disposed above the floor, the first base configured to support a robotic arm thereon and including a plurality of casters attached thereto to allow the surgical robotic cart assembly to move along the floor;
    a second base interposed between the first base and the floor, wherein the second base is parallel to the first base;
    at least one vacuum cup coupled to the second base;
    an actuator configured to move the second base and the at least one vacuum cup away from the first base and towards the floor to engage the at least one vacuum cup with the floor; and
    a vacuum source in fluid communication with the at least one vacuum cup and configured to remove air from the at least one vacuum cup thereby securing the at least one vacuum cup to the floor, when the at least one vacuum cup is in contact with the floor, and immobilizing the surgical robotic cart assembly.

2. The surgical robotic cart assembly of claim 1, further comprising a pedal switch to actuate the actuator, wherein the pedal switch moves the second base and the at least one actuator from a first position, above the floor, towards a second position, on the floor, thereby lowering the second base and the at least one vacuum cup towards the floor.

3. The surgical robotic cart assembly of claim 2, wherein the pedal switch moves the second base and the actuator from the second position, on the floor, towards the first position, above the floor, thereby lifting the at least one vacuum cup away from the floor.

4. The surgical robotic cart assembly of claim 2, further comprising a vacuum manifold coupled to the at least one vacuum cup in fluid communication with the vacuum manifold, the at least one vacuum cup being in fluid communication with the vacuum source via the vacuum manifold.

5. The surgical robotic cart assembly of claim 4, wherein the at least one vacuum cup is positioned around a perimeter of the second base.

6. The surgical robotic cart assembly of claim 4, wherein the at least one vacuum cup is disposed over the second base about a perimeter thereof.

7. The surgical robotic cart assembly of claim 4, wherein when the at least one vacuum cup is in contact with the floor, actuation of the vacuum source sealingly engages the at least one vacuum cup to the floor.

8. The surgical robotic cart assembly of claim 7, wherein the surgical robotic cart assembly is immobile when the at least one vacuum cup is sealingly engaged to the floor.

9. The surgical robotic cart assembly of claim 1, further comprising a biasing member interposed between the first base and the at least one vacuum cup, wherein the biasing member is configured to urge the at least one vacuum cup towards the first base.

10. A surgical robotic cart assembly supported on a floor, the surgical robotic cart comprising:
    a base assembly including:
        a first base disposed above the floor and a second base interposed between the first base and the floor such that the second base is parallel to the first base, the second base being secured to the first base by at least one hydraulic actuator; and
    an immobilization assembly coupled to the base assembly, the immobilization assembly having a vacuum source and at least one vacuum cup coupled to the second base, the at least one vacuum cup being in fluid communication with the vacuum source, wherein the vacuum source is configured to remove air from the at least one vacuum cup, when the at least one vacuum is in contact with the floor, and sealingly engage the at least one vacuum cup to a floor thereby immobilizing the surgical robotic cart assembly.

11. The surgical robotic cart assembly of claim 10, wherein the immobilization assembly further includes a pedal switch to actuate the hydraulic actuator, wherein the pedal switch moves the at least one hydraulic actuator from a second position towards a first position thereby lifting the second base relative to the floor and moving each vacuum cup away from the floor.

12. The surgical robotic cart assembly of claim 11, wherein the at least one vacuum cup is coupled to a second surface of the second base.

13. The surgical robotic cart assembly of claim 12, wherein a first actuation of the pedal switch moves the at least one hydraulic actuator from a first position to a second position thereby lowering the second base relative to the floor and placing the at least one vacuum cup in contact with the floor.

14. The surgical robotic cart assembly of claim 13, wherein when the at least one vacuum cup is in contact with the floor, actuation of the vacuum source sealingly engages the at least one vacuum cup to the floor.

15. The surgical robotic cart assembly of claim 14, wherein a second actuation of the pedal switch moves the at least one hydraulic actuator from the second position to the first position thereby lifting the second base relative to the floor and moving the at least one vacuum cup away from the floor.

\* \* \* \* \*